July 27, 1954 H. C. SWIM Plant Pat. 1,292
ROSE PLANT
Filed June 29, 1953
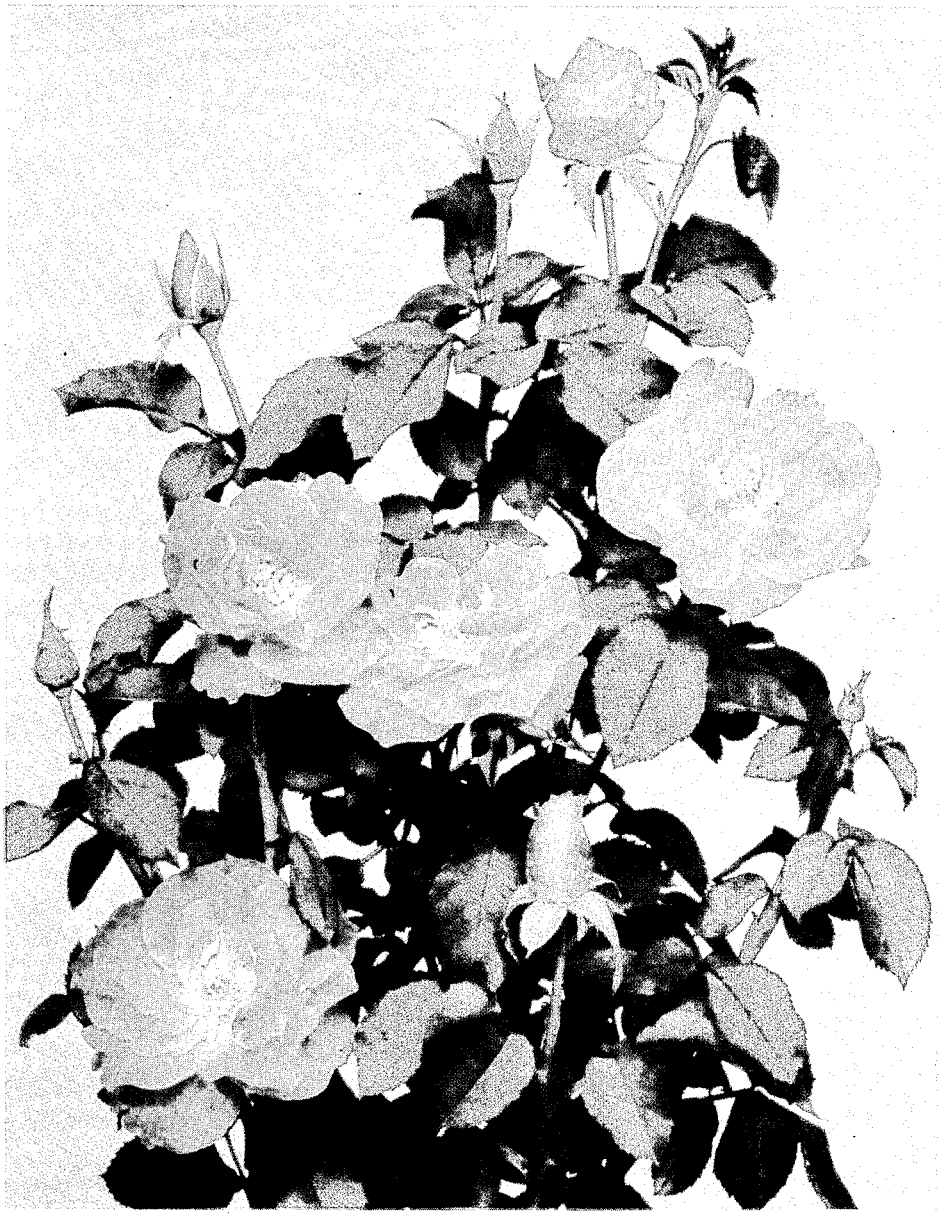
Inventor
H. C. Swim
By: Robert Cobb
Attorneys Patented July 27, 1954

Plant Pat. 1,292

UNITED STATES PATENT OFFICE 1,292

ROSE PLANT

Herbert C. Swim, Ontario, Calif., assignor to Armstrong Nurseries, Inc., Ontario, Calif., a corporation of California Application June 29, 1953, Serial No. 364,975

1 Claim. (Cl. 47—61)

The present invention relates to a new and distinct variety of rose plant of the hybrid polyantha class, which was originated by me by crossing the variety "Minna Kordes," better known in the United States as "World's Fair" (Plant Patent No. 362) with the variety "Pinocchio" (Plant Patent No. 484).

The primary objective in making this cross was to produce a new variety of rose plant which combines the best characteristics of the two parent varieties. This objective was fully achieved, as evidenced by the fact that my new variety is endowed with the following unique combination of outstanding characteristics:

(1) The blooms of my new variety are produced in clusters of several flowers per cluster, which is a characteristic trait of the pollen parent "Pinocchio";

(2) The blooms of the new variety have very good petal substance, as inherited from "Pinocchio," with attendant lasting quality of the blooms;

(3) The flower size falls between that of the two parents; and (4) The color of the flowers of my new variety is a medium shade of red, approaching that of "World's Fair," but is a lighter and brighter red than that of "World's Fair."

In comparison with its seed parent "World's Fair," the plant habit of my new variety is upright, whereas that of "World's Fair" is more spreading; the flowers of the new variety are produced in clusters, with substantially more flowers per cluster than are produced by "World's Fair;" the flower color of my new variety is a medium shade of red, whereas that of "World's Fair" is a deep shade of red; and the petal substance of my new variety is substantially greater and better than that of "World's Fair."

As compared with its pollen parent "Pinocchio," the plant habit of my new variety is narrow, upright and compact, whereas that of "Pinocchio" is more spreading and less compact; the foliage of my new variety is abundant and covers the plant well, whereas the foliage of "Pinocchio" is less abundant and does not cover the plant completely; the flower color of the new variety is a medium shade of red, whereas that of "Pinocchio" is pink suffused salmon; and the size of the flowers of my new variety is greater than that of "Pinocchio," averaging between 2¼ to 2¾ inches in diameter, whereas that of "Pinocchio" is usually about 2 inches in diameter when grown under comparable cultural conditions at Ontario, California.

Asexual reproduction of my new variety by budding at Ontario, California, shows that the foregoing characteristics and distinctions come true to form and are established and transmitted through succeeding propagations.

The accompanying drawing shows typical specimens of the flowers, foliage and stems of my new variety, with the colors thereof depicted as nearly true as it is reasonably possible to make the same in a color illustration of this character.

The following is a detailed description of my new variety, with color terminology in accordance with Robert F. Wilson's Horticultural Colour Chart (hereinafter identified as "Wilson") and with Ridgway's Color Standards and Nomenclature (hereinafter identified as "Ridgway"):

Type: Bush; outdoor; seedling; for garden decoration.

Class: Hybrid polyantha.

Breeding: Seedling.

*Seed parent.*—"World's Fair."

*Pollen parent.*—"Pinocchio."

Propagation: Holds its distinguishing characteristics through succeeding propagations by budding.

*Flower*

Locality where grown and observed: Ontario, California.

Flowers borne: Usually five or more to stem; in regular, somewhat rounded clusters; on strong, long stems.

Quantity of bloom: Free to abundant outdoors.

Continuity: More or less continuous during growing season.

Fragrance: None to slight.

Bud:

*Peduncle.*—Average length; average caliper; erect; smooth; numerous gland-tipped cilia and few hairs. Color—near Lettuce Green, Plate V (Ridgway), shaded somewhat with between Deep Corinthian Red, Plate XXVII (Ridgway) and Indian Red, Plate XXVII (Ridgway) on side exposed to sun.

*Before calyx breaks.* — Size — medium. Form—medium length; ovoid; with foliaceous appendages; some tomentum and few gland-tipped cilia on the surface of the bud; usually without foliaceous parts extending beyond the tip of the bud.

*As calyx breaks.*—Color—between Currant Red, Plate 821, page 167 (Wilson) and

Cardinal Red, Plate 822/3, page 168 (Wilson).

*Sepals.*—Inner surface—with fine, woolly tomentum. Margins—alternate sepals lined with fine, woolly tomentum; others lined with stipitate glands.

*As first petal opens.*—Size—average. Form—medium length; ovoid. Color—outside—near Currant Red, Plate 821/3, page 167 (Wilson); small area at base of petals near attachment near Aureolin, Plate 3/2, page 3 (Wilson). Inside—Between Cherry, Plate 722, page 157 (Wilson) and Currant Red, Plate 821/1, page 167 (Wilson); small area at base of petal near attachment near Aureolin, Plate 3/2, page 3 (Wilson).

*Opening.*—Opens up well; is not retarded from opening by cold, hot, wet or dry weather.

Bloom:

*Size (when fully open).*—Average; 2¼ to 2¾ inches.

*Petalage.*—Semi-double; from 15 to 20 petals, plus 4 to 7 petaloids; arranged regularly.

*Form.*—High-centered at first; becoming open later; petals at first being cupped, with lateral margins only slightly reflexed ¼ of upper portion of petals; outermost petals with lateral margins sometimes reflexed ½ of upper portion of petal; apex of outermost petals sometimes reflexed ¼ of petal length; becoming later at maturity flat-cupped, with lateral margins of petals usually only slightly reflexed ½ to ¾ of length of petal; apex sometimes reflexed ⅛ to ¼ of petal length.

Petals:

*Texture.*—Thick; leathery; with inside velvety and outside satiny.

*Shape.*—Outside—broadly obovate, with apex somewhat flat; rarely with 1 or 2 notches. Intermediate—obovate, with apex rounded; sometimes with 1 or 2 notches. Inside—narrowly obovate, with apex rounded; sometimes with 1 or 2 notches.

This description of a newly opened flower was made from a rose grown outdoors in the month of October, at Ontario, California:

*Color.*—Outside petal—outside surface—between Turkey Red, Plate 721/3, page 94 (Wilson) and Cherry, Plate 722/2, page 157 (Wilson); small area at base of petal near attachment near Aureolin, Plate 3/3, page 3 (Wilson). Inside surface—between Turkey Red, Plate 721/2, page 94 (Wilson) and Cherry, Plate 722/1, page 157 (Wilson); small area at base of petal near attachment near Aureolin, Plate 3/2, page 3 (Wilson). Intermediate petal—outside surface—between Turkey Red, Plate 721/3, page 94 (Wilson) and Cherry, Plate 722/2, page 157 (Wilson); small area at base of petal near attachment near Aureolin, Plate 3/2, page 3 (Wilson). Inside surface—between Turkey Red, Plate 721/2, page 94 (Wilson) and Cherry, Plate 722/1, page 157 (Wilson); small area at base of petal near attachment near Aureolin, Plate 3/2, page 3 (Wilson). Inner petal—outside surface—between Turkey Red, Plate 721/3, page 94 (Wilson) and Cherry, Plate 722/2, page 157 (Wilson); small area at base of petal near attachment near Aureolin, Plate 3/2, page 3 (Wilson). Inside surface—between Turkey Red, Plate 721/2, page 94 (Wilson) and Cherry, Plate 722/1, page 157 (Wilson); small area at base of petal near attachment near Aureolin, Plate 3/2, page 3 (Wilson).

This description was made from a rose that was open for three days outdoors in the month of October, at Ontario, California:

*Color.*—Outside petal—outside surface—between Rose Madder, Plate 23, page 23 (Wilson) and Rose Red, Plate 724/2, page 158 (Wilson); small area at base of petal near attachment near Aureolin, Plate 3/3, page 3 (Wilson). Inside surface—near Rose Red, Plate 724/1, page 158 (Wilson), with upper ¼ to ⅓ of petal shaded toward apex with near Currant Red, Plate 821/3, page 167 (Wilson); small area at base of petal near attachment near Aureolin, Plate 3/3, page 3 (Wilson). Inside petal—outside surface—between Rose Madder, Plate 23, page 23 (Wilson) and Rose Red, Plate 724/1, page 158 (Wilson); small area at base of petal near attachment near Aureolin, Plate 3/3, page 3 (Wilson). Inside surface—near Currant Red, Plate 821/2, page 167 (Wilson); small area at base of petal near attachment near Aureolin, Plate 3/3, page 3 (Wilson).

*General color effect.*—Newly opened flower—between Turkey Red, Plate 721/1, page 94 (Wilson) and Cherry, Plate 722/1, page 157 (Wilson). 3 days open—between Rose Red, Plate 724, page 158 (Wilson) and Currant Red, Plate 821/3, page 167 (Wilson); small area at base of petal near attachment near Aureolin, Plate 3/3, page 3 (Wilson).

*Behavior.*—Drop off cleanly; not particularly affected by cold, hot, wet or dry weather.

*Flower longevity.*—On bush in garden—4 to 5 days in October. Cut roses grown outdoors kept at living-room temperatures—4 to 5 days in October.

*Reproductive organs*

Stamens: Average number to many; arranged regularly about pistils.

Filaments: Short to medium length; 3 to 7 mm. in length; most with anthers. Color—between Canary Yellow, Plate 2/1, page 2 (Wilson) and Aureolin, Plate 3/1, page 3 (Wilson).

Anthers: Small to medium size; all open approximately at once. Color—upper side—margins near Indian Yellow, Plate 6/2, page 6 (Wilson); remainder near Canary Yellow, Plate 2/3, page 2 (Wilson). Under side—margins between Indian Yellow, Plate 6/2, page 6 (Wilson) and Indian Yellow, Plate 6/3, page 6 (Wilson); remainder near Canary Yellow, Plate 2/3, page 2 (Wilson).

Pollen: Abundant. Color—near Saffron Yellow, Pate 7, page 7 (Wilson).

Pistils: Few; approximately 40 in number.

Styles: Moderately even; average length; thin to average caliper; somewhat separated; 4 to 8 mm. in length. Color—upper ½ of style near Carmine, Plate 21/1, page 21 (Wilson); lower ½ near Uranium Green, Plate 63/3, page 63 (Wilson).

Stigma: Color—between Aureolin, Plate 3/3, page 3 (Wilson) and Lemon Yellow, Plate 4/3, page 4 (Wilson).

Ovaries: Most enclosed in but some protruding from calyx.

Hips: Average length; globular; smooth; walls moderately thick, fleshy. Color (⅔ mature)—between Kildare Green, Plate XXXI (Ridgway) and Absinthe Green, Plate XXXI (Ridgway); shaded somewhat with near Mineral Red, Plate XXVII (Ridgway).

Sepals: Permanent; medium length; recurved. Color—inside near Biscay Green, Plate XVII (Ridgway); masked by White woolly tomentum. Outside—between Courge Green, Plate XVII (Ridgway) and Biscay Green, Plate XVII (Ridgway); shaded with near Mineral Red, Plate XXVII (Ridgway).

Seeds: Few; medium size; 6 to 12 in number.

*Plant*

Foliage:

*Leaves.*—Compound of usually 5 to 7, sometimes 9 leaflets; abundant; medium size to large; moderately heavy; leathery and semi-glossy.

*Leaflets.*—Shape—ovoid, with acute apex and round base. Margin—simply serrate.

*Color.*—Mature: upper surface — between Deep Dull Yellow-Green (1) Plate XXXII (Ridgway) and Dark Dull Yellow-Green, Plate XXXII (Ridgway); under surface—between Turtle Green, Plate XXXII (Ridgway) and Chromium Green, Plate XXXII (Ridgway). Young: upper surface—between Mineral Red, Plate XXVII (Ridgway) and Dark Mineral Red, Plate XXVII (Ridgway); under surface—near Mineral Red, Plate XXVII (Ridgway).

*Rachis (the supporting stem of the compound leaf).*—Average size. Upper side—grooved; hairy; with many stipitate glands on edges. Under side—prickly and with some stipitate glands.

*Stipules.*—Medium length; medium width to wide; short to medium length points turning out at an angle of more than 45°; sometimes recurved slightly toward the stem.

*Disease.*—Average resistance to mildew, as compared with other varieties grown under comparable cultural conditions at Ontario, California.

Growth:

*Habit.*—Bushy; upright; much-branched.

*Growth.*—Vigorous.

*Canes.*—Medium caliper to heavy.

*Main stems.*—Color—between Oil Green, Plate V (Ridgway) and Lettuce Green, Plate V (Ridgway). Large prickles—several to many; medium length; hooked slightly downward; with medium length, moderately broad base. Color—near Russet, Plate XV (Ridgway). Small prickles—few. Color—between Russet, Plate XV (Ridgway) and Cinnamon-Brown, Plate XV (Ridgway). Hairs—none.

*Branches.*—Color—between Lettuce Green, Plate V (Ridgway) and Parrot Green, Plate VI (Ridgway). Large prickles—several; medium length; hooked slightly downward; with medium length, moderately broad base. Color—between Russet, Plate XV (Ridgway) and Cinnamon-Brown, Plate XV (Ridgway). Small prickles—few to several. Color—between Russet, Plate XV (Ridgway) and Cinnamon-Brown, Plate XV (Ridgway). Hairs—none.

*New shoots.*—Color—near Courge Green, Plate XVII (Ridgway), shaded with between Mineral Red, Plate XXVII (Ridgway) and Indian Red, Plate XXVII (Ridgway). Large prickles—several; medium length; hooked slightly downward; with medium length, moderately broad base. Color—near Kildare Green, Plate XXXI (Ridgway), shaded with near Hydrangea Red, Plate XXVII (Ridgway). Small prickles—few to several. Color—near Hydrangea Red, Plate XXVII (Ridgway). Hairs—none.

I claim:

A new and distinct variety of rose plant of the hybrid polyantha class, substantially as herein shown and described, characterized particularly as to novelty by its cluster blooming habit, by the improved petal substance and attendant lasting quality of its blooms, by the relatively good size of its flowers ranging between that of its parents, and by the distinctive medium red general color tonality of its flowers, approaching the coloring of the flowers of its parent "World's Fair" (Plant Patent No. 362) but lighter and brighter than the coloring of the latter.

No references cited.